(12) United States Patent
Carnell (10) Patent No.: US 6,861,047 B1
(45) Date of Patent: Mar. 1, 2005

(54) ORAL HYGIENE PREPARATIONS; ASSOCIATED METHODS AND KIT

(76) Inventor: Victor Carnell, 1529 E. 36th St., Spokane, WA (US) 99203

(*) Notice: Subject to any disclaimer, the term of this patent is extended or adjusted under 35 U.S.C. 154(b) by 0 days.

(21) Appl. No.: 09/890,135

(22) PCT Filed: Jan. 26, 2000

(86) PCT No.: PCT/US00/01952

§ 371 (c)(1),
(2), (4) Date: Nov. 5, 2001

(87) PCT Pub. No.: WO00/44338

PCT Pub. Date: Aug. 3, 2000

Related U.S. Application Data (63) Continuation-in-part of application No. 09/239,051, filed on Jan. 27, 1999, now abandoned.

(51) Int. Cl.[7] ................................................. A61K 7/16
(52) U.S. Cl. .......................................... 424/49; 424/52
(58) Field of Search ..................... 424/49, 52; 433/216

(56) References Cited

U.S. PATENT DOCUMENTS

| | | | | |
|---|---|---|---|---|
| 4,205,061 | A | | 5/1980 | Vidra ........................... 424/55 |
| 4,666,708 | A | * | 5/1987 | Goldemberg et al. .......... 424/49 |
| 4,721,614 | A | * | 1/1988 | Winston et al. ................ 424/52 |
| 4,915,219 | A | | 4/1990 | Ottimo .................... 206/209.1 |
| 5,380,648 | A | | 1/1995 | Elango et al. .............. 435/7.32 |
| 5,624,906 | A | * | 4/1997 | Vermeer ........................ 514/23 |
| 5,880,076 | A | * | 3/1999 | Vermeer ...................... 510/123 |
| 2002/0086039 | A1 | * | 7/2002 | Lee et al. .................... 424/401 |
| 2003/0039617 | A1 | * | 2/2003 | White et al. ................... 424/49 |

OTHER PUBLICATIONS

Caudry S. Contaminated Toothbrushes and Their Disinfection. J of Infection Control 61(6)511–?, Jun. 1995.*
Meier S. An In vitro Investigation of the Efficacy of CPC for Use in Toothbrush Decontamination. J of Dental Hygiene 70(4)161–165, Jul.–Aug. 1996.*
Caudry S. D. et al. "Contaminated Toothbrushes and Their Disinfection" Journal of Intection Control. Jun. 1995. vol. 61, No. 6, pp. 511–513.
Meier S. et al.; "An In Vitro Investigation of the Efficacy of CPC for Use in Toothbrush Decontamination." Journal of Dental Hygiene. Jul.–Aug. 1996. vol. 70, No. 4, pp. 161–165.
Invittox Protocol No. 99 "Red Blood Cell Lysis and Protein Denaturation", Jun. 1994.
Copy of the International Search Report dated May 25, 2000.

* cited by examiner

*Primary Examiner*—Ralph Gitomer
(74) *Attorney, Agent, or Firm*—Nields & Lemack (57) ABSTRACT

Oral hygiene preparations, an associated method, and kit for utilizing same is disclosed and wherein the oral hygiene preparations reduce the incidence of caries in patients, including immunocompromised and chemotherapy treated patients. The method includes contacting the patient's teeth and surrounding oral cavity with a toothpaste and mouthwash composition comprising a therapeutically effective amount of Cetyl Pyridinium Chloride and Dehydroacetic Acid; and exposing the patient's dental appliances and toothbrush periodically to a disinfecting solution comprising a therapeutically effective amount of Cetyl Pyridinium Chloride and Dehydroacetic Acid.

9 Claims, 2 Drawing Sheets

ORAL HYGIENE PREPARATIONS; ASSOCIATED METHODS AND KIT

This application is a National Stage application filed under Rule 371 based on application PCT/US00/01952 filed Jan. 26, 2000, which claims priority to CIP U.S. application Ser. No. 09/239,051 filed Jan. 27, 1999, now abandoned.

TECHNICAL FIELD

This invention relates generally to hygiene preparations, particularly for oral care, but: also for other applications in the treatment of hair or skin. The invention pertains to compositions that 1) inhibit the development of caries and 2) are less toxic or irritant to oral tissues in human patients including immunocompromised and chemotherapy treated patients. In addition, the invention pertains to an oral hygiene kit, which includes a toothpaste, a mouthwash, and disinfectant solution, which in combination, reduces the incidence of caries by the bacterial flora that contribute to the development of this and other disorders.

BACKGROUND ART

The removal of food/oral debris, the minimization of the microbial population in the mouth and throat, and the removal and prevention of plaque and calculus deposition are important for the enhancement of personal feelings of well-being (clean breath, mouth taste and mouth feel) and the prevention of oral diseases. Since the oral environment is conducive to microbial growth and subject to the reintroduction of food and microorganisms, and because plaque and calculus are continually being deposited on teeth, ideal oral hygiene methods and compositions must be a) capable of good cleansing and microbial knockdowns, b) able to remove plaque and calculus and prevent their formation, and c) convenient and safe for repetitive use.

Traditional mouth washes and dentrifices suffer in all three areas.

The prior art is replete with numerous prior art references which are directed to various dentifrices, dentifricating paste, powders, and liquids which are employed for cleaning the teeth. As a general matter, these dentifrices contain a mixture of various ingredients including such materials as polishing agents and abrasives for scouring and scrubbing the teeth, and which are further operable, to some degree, to neutralize various acids present in the gaps between the teeth. These same substances further inhibit, to some extent, the subsequent growth of various forms of bacteria that contribute to the development of caries and other disorders.

While the prior art compositions, and other methods have operated with varying degrees of success in controlling the onset of caries, these same methods and compositions have not been particularly useful in arresting oral and other systemic diseases which are caused by bacteria and fungi which may be introduced by way of, or are resident in, the patient's oral cavity.

In addition to the above, it is known that because it is essential that the immuno-compromised patient maintain optimum weight, the frequent eating of high-calorie meals is encouraged. It is not advisable to restrict sugar and starches as it deprives the patient of essential calories.

Adults receiving radiation of the head and neck for oncological therapy present a unique situation with damage to the mucosal, and skeletal tissues, in addition to the frequently seen radiation caries of the dentin. Of equal importance is the concern of orthodontists regarding the decalcification of tooth enamel during orthodontic treatment, which is so prevalent today. Seniors are experiencing rampant root surface decay to the extent it is now nearly epidemic.

Today's regimen of brushing with current toothpaste's and rinses with high fluoride concentrations are not able to curb the acid production of carbohydrates that feed the dental plaque resulting in high decay rates and periodontal disease.

It is widely accepted, for example, that the best method for inhibiting canes is to refrain from foods containing high amounts of refined carbohydrates such as sucrose; fluoride treatment for developing teeth; and the subsequent mechanical removal of plaque by daily oral hygiene. On the other hand, there are no generally well accepted techniques, or preparations that are normally employed to inhibit many of the oral cavity disorders which are associated with many pathogenic bacterial, viral, and fungal agents. Additionally, many of the bacterial, viral and fungal pathogens produce, or encourage the production of a variety of enzymes which have been suspected as having a role in some periodontal maladies which have, as one of their many symptoms, tissue destruction; gingival inflammation; phagocytosis; bone resorption; and a variety of other deleterious conditions.

The invention pertains to compositions that:

1) inhibit the development of caries and 2) are less toxic or irritant to oral tissues in human patients including immunocompromised and chemotherapy treated patients.

These compositions are comprised of varying concentrations of Cetylpyridinium Chloride (CPC) and dehydroacetic acid (DHA). In addition, the invention pertains to an oral hygiene kit that includes a toothpaste, mouthwash, and disinfectant solution, which in combination, reduces the incidence of caries by reducing the bacterial flora that contributes to the development of this and other disorders. The invention also pertains to compositions that are useful for the care of hair (e.g., shampoos) and skin (e.g., soap and gels, lotions and creams).

BRIEF DESCRIPTION OF DRAWINGS

Preferred embodiments of the invention are described below with reference to the following accompanying drawings.

MODES FOR CARRYING OUT THE INVENTION

In accordance with one aspect of the present invention, an oral hygiene method is disclosed which reduces the incidence of caries and is less toxic and irritant to oral tissues in a patient and which includes; contacting the patient's teeth and surrounding oral cavity with a toothpaste, and mouthwash composition comprising a therapeutically effective amount of Cetylpyridinium Chloride; and exposing the patient's dental appliances and toothbrush periodically to a disinfecting solution comprising a therapeutically effective amount of Cetylpyridinium Chloride.

Still further, another aspect of the present invention is to provide an oral hygiene kit which includes: a toothpaste for use in combination with a toothbrush; a mouthwash; and a disinfecting solution to disinfect the toothbrush, and wherein the toothpaste, mouthwash and disinfecting solution each comprise a therapeutically effective amount of Cetylpyridinium Chloride and Sodium Lauroyl Sarcosinate to reduce the incidence of caries in a patient.

Yet still another aspect of the present invention relates to an oral hygiene kit that comprises a toothpaste comprising less than about 0.37%, by weight, of Cetylpyridinium Chloride and less than about 2.6%, by weight, of Sodium Lauroyl Sarcosinate; a mouthwash comprising less than about 0.4%, by weight, of Cetylpyridinium Chloride and less than about 0.4%, by weight, of Sodium Lauroyl Sarcosinate; and a disinfecting solution comprising less than about 0.075% by weight, of Cetylpyridinium Chloride and less than about 2.1%, by weight, of Sodium Lauroyl Sarcosinate.

More specifically, the oral hygiene preparations and kit utilizing same includes a toothpaste that consists essentially of: about 1.6% to about 2.6% by weight of Sodium Lauroyl Sarcosinate;

about 0.25% to about 0.30% by weight of Sodium Fluoride;

about 0.1% to about 0.6% by weight of Dehydroacetic Acid;

about 0.18% to about 0.37% by weight of Cetylpyridinium Chloride;

about 30% to about 60% by weight of Sorbitol;

about 3% to about 10% by weight of Glycerin;

about 1% to about 3% by weight of Cellulose Gum;

about 0.3% to about 1.0% by weight of Titanium Dioxide;

about 0.08% to about 0.1% by weight of Flavors;

about 10% to about 30% by weight of Hydrated Silica; and about 10% to about 30% by weight of water.

In addition to the foregoing, the oral hygiene preparations and the kit utilizing same includes a mouthwash which consists essentially of:

about 0.15% to about 0.4%, by weight, of Sodium Lauroyl Sarcosinate;

about 0.25% to about 0.30%, by weight, of Sodium Fluoride;

about 0.01% to about 0.06%, by weight of Dehydroacetic Acid;

about 0.05% to about 0.10%, by weight of Cetylpyridinium Chloride;

about 5% to about 10% by weight of Sorbitol;

about 10% to about 20% by weight of Glycerin;

about 0.01% to about 0.1%, by weight, of Menthol;

about 0.01% to about 0.1%, by weight, of citric acid;

about 0.01% to about 1.0%, by weight, of a Polysorbate;

about 0.008% to about 0.1% by weight of Potassium Tribasic Phosphate;

about 0.01% to about 0.10%, by weight, of Potassium Benzoate;

about 0.1% to about 0.7%, by weight, of Peppermint oils; and about 70% to about 80%, by weight, of water.

Yet, still further, the oral hygiene preparations and kit utilizing same includes a disinfecting solution which consists essentially of:

about 0.06% to about 0.75% by weight of Cetylpyridinium Chloride;

about 1% to about 2% by weight of Sodium Lauroyl Sarcosinate;

about 0.01% to about 2% by weight of Sodium Carbonate;

about 14% to about 357% by weight of ethanol;

about 0.01% to about 0.075% by weight of EDTA; and about 65% to about 87% by weight of water.

The preferred embodiment of the present invention for toothpaste is comprised of about 1.7% by weight of Sodium Lauroyl Sarcosinate; about 0.25% by weight of Sodium Fluoride; about 0.2% by weight of Dehydroacetic Acid; about 0.30% by weight Glycerin, at a pH of 6.2 (hereafter referred to as TP-1).

The preferred embodiment of the present invention for mouthwash is comprised of about 0.2% by weight of Sodium Lauroyl Sarcosinate; about 0.25% by weight of Sodium Fluoride; about 0.1% by weight of Dehydroacetic Acid; about 0.05% by weight of Cetylpyridinium Chloride; at a pH of 6.2 (hereafter referred to as MW-1).

Figure 1:
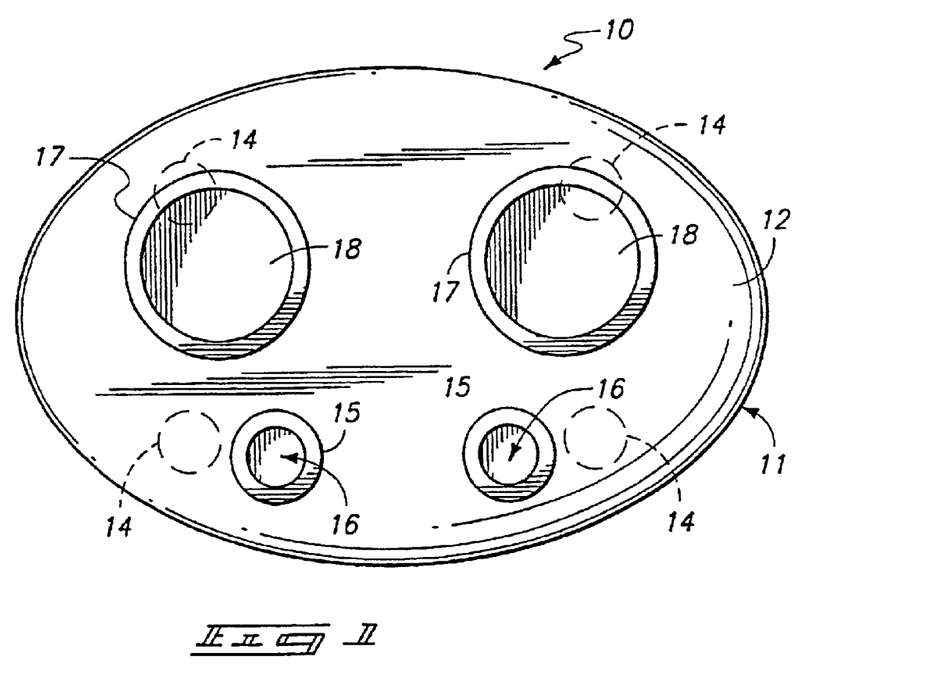
FIG. 1 is a plan view of an assembly that is utilized in connection with the present invention.
Figure 2:
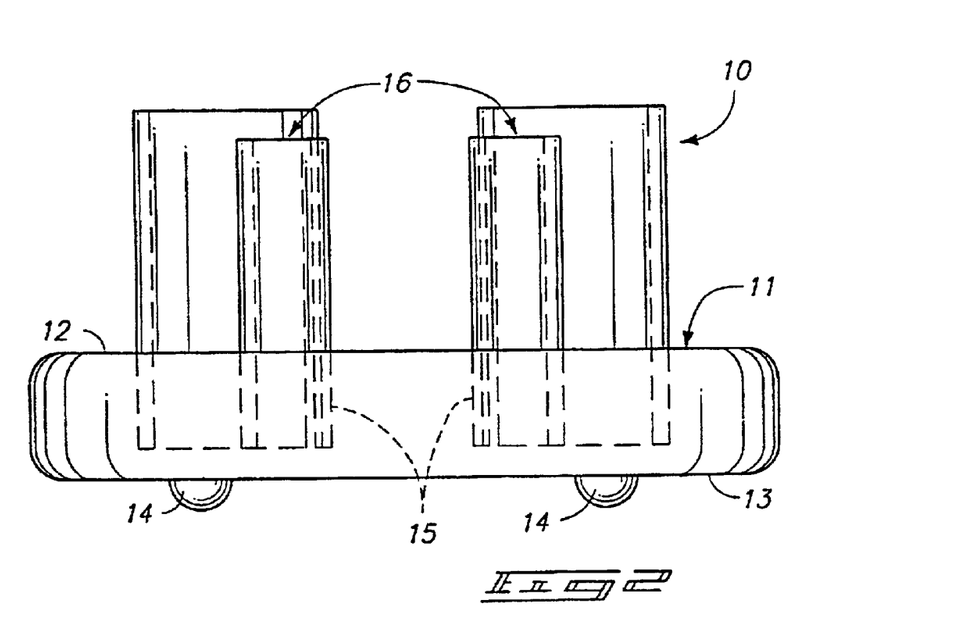
FIG. 2 is a front elevation view of the assembly shown in FIG. 1.
Figure 3:
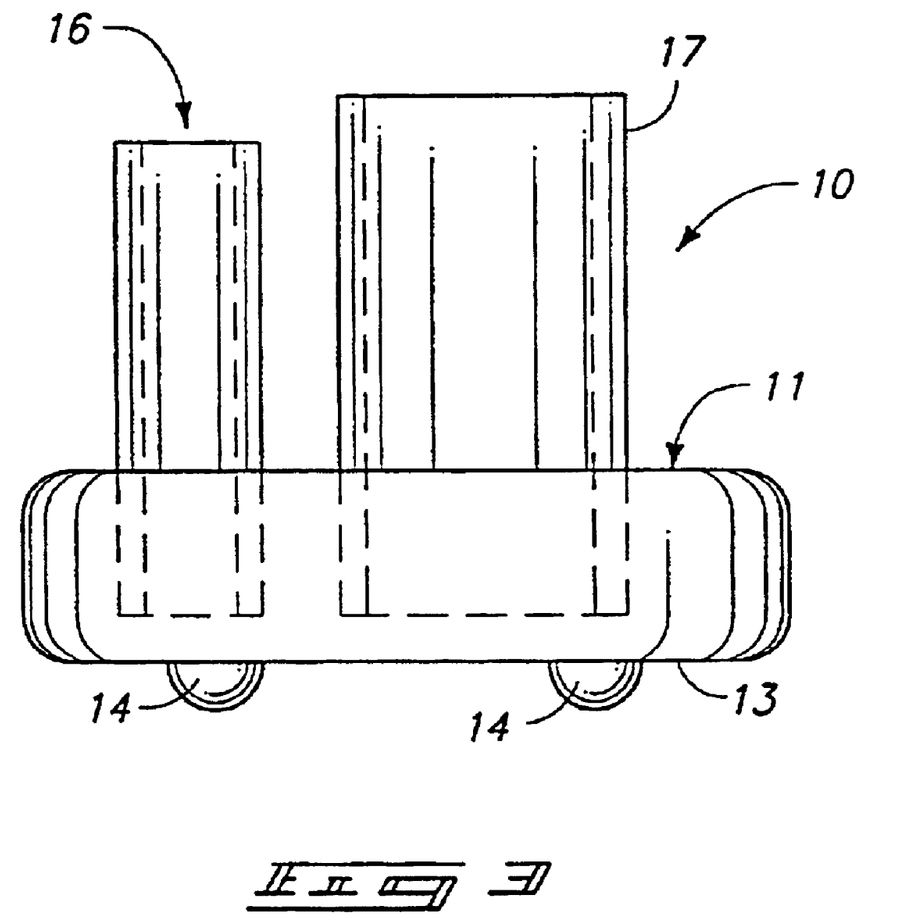
FIG. 3 is a side elevation view of the assembly shown in FIG. 1.

An apparatus used in the implementation of the present oral hygiene preparations and associated kit is shown in FIGS. 1, 2 and 3, respectively. As shown therein, an assembly for holding both a toothbrush, and the aforementioned disinfecting solution is illustrated. The assembly 10 includes a base number 11 which includes a top surface 12 and an opposed bottom surface 13. Made integral with the bottom surface are small protrusions or feet 14 which engage a supporting surface not shown. Extending substantially normally upwardly relative to the top surface 112 are a pair of toothbrush holders 15 which define a cavity 16 which will receive the handle of a toothbrush (not shown). A pair of disinfectant solution containers 17 are provided which define individual cavities 18. The disinfecting solution is placed in these cavities and the toothbrush bristles are immersed in same for given periods of time to rid them of various bacterial, viral and fungal pathogens.

INDUSTRIAL APPLICABILITY

In order to demonstrate the novelty and efficacy of the present oral hygiene preparations and the kit utilizing same, the following examples are provided below.

EXAMPLE 1

To demonstrate the efficacy of the aforementioned toothpaste, the following experiments were performed.

Experiment 1.

In this experiment, 100–150 milligrams of the aforementioned toothpaste composition was suspended in sterile distilled water. The solution was vortexed to make a suspension. This was later transferred to a sterile cup. A tooth was provided and submerged in the toothpaste suspension for a period of three minutes. Following the submersion of the tooth, it was removed and rinsed thoroughly with sterile distilled water. Excess water was removed by shaking the tooth.

Thereafter, the tooth was placed on a blood agar plate that bad been inoculated with a lawn, of *Staphlycoccus mutans* (1.5×108 CFU/ml). Thereafter, the blood agar plate was incubated at a temperature of about 35 degrees C. for 24 hours. The plate was then observed with respect to the inhibition of bacterial growth around the tooth. Thereafter, the zone of inhibition was measured in millimeters, and the results were recorded.

Experiment 2.

In this experiment, 100–150 milligrams of toothpaste (TP-1) was placed in sterile distilled water and subsequently vortexed to provide a suspension. This suspension was later transferred to a sterile cup. A tooth was submerged in the toothpaste suspension for three minutes. Thereafter, the tooth was thoroughly rinsed with distilled water and the excess water was removed from the tooth. The tooth was then transferred to a sterile cup which contained the aforementioned mouthwash solution. The tooth was submerged in the mouthwash solution for one minute, and then later removed and excess mouthwash was removed from same. The tooth was then placed on a blood agar plate that had been inoculated with a lawn of *S. mutans*, and *Candida albicans* ($1.5 \times 10^8$ CFU/ml). The blood agar plate was then incubated for a period of 24 hours at a temperature of 35 degrees C., and the plate was observed for the inhibition of bacterial growth around the tooth. This zone of inhibition, in millimeters was then measured, and the results recorded.

Experiment 3

In this experiment, 100–150 milligrams of toothpaste (TP-1) was placed in sterile distilled water and a vortexed was applied to same to create a suspension. This suspension was transferred to a sterile cup. A tooth was later placed in the toothpaste suspension for three minutes. The tooth was removed and sterile water was applied to the same. Excess water was removed from the tooth. The tooth was then transferred to the cup and the tooth subsequently submerged in the mouthwash (MW-1) [a sterile] solution for one minute. The tooth was then removed and rinsed thoroughly with sterile distilled water. The tooth was then placed on a blood agar plate that had been inoculated with a lawn of *Candida* ($1.5 \times 10^8$ CFU/ml). This plate was then incubated at 35 degrees C. for 24 hours. The plate was subsequently observed for the inhibition of bacterial growth around the tooth. The estimated zone of inhibition was then measured, in millimeters, and the results recorded.

In each of the three experiments noted above, inhibition was measured at both 16 hours and at 24 hours. The results revealed that a zone of inhibition was observed around each of the teeth. This zone of inhibition ranged in size from two to five millimeters. These results demonstrate that the toothpaste, and the toothpaste and mouthwash combination provided inhibition against the organisms noted above. These organisms are common pathogens in the oral cavities of humans.

EXAMPLE 2

In this example, the efficacy of the disinfecting solution was explored. Inoculums ($1.5 \times 10^8$ CFU/ml (Test A) and $1.5 \times 10^4$ CFU/ml (Test B) of *S. mutans* ATCC 35668; *S. aureus* ATCC 25923; and *C. albicans* were prepared and vortexed. Each inoculum was poured into separate sterile cups. Thereafter, a patient's toothbrush was placed in each of the inoculums and completely submerged for 10 seconds. Following instructions, the toothbrushes were removed from the inoculums and excess inoculum was removed from each of the brushes. Thereafter, the respective brushes were submerged in the disinfecting solution earlier described, and a timing sequence was initiated. Thereafter, the brushes were removed at 5 minutes, 30 minute, 10 minute, 30 minute and 60 minutes intervals. Each of these brushes were then placed in a 10 millimeter nutrient broth, when testing, for the *S. aureus* and *C. albicans*; and 10 millimeters of Todd Hewitt broth, when testing, for the organism *S. mutans*. The tubes of nutrient, and Todd Hewitt broth and brushes were then vortexed and 0.01 millimeters of inoculant was removed from the respective suspension and inoculated onto separate blood agar plates. A loop was used to streak the individual blood agar plates for isolation. The blood agar plates were incubated for periods of 24, 48 and 72 hours and subsequent records were made of the colony counts at each of these points in time. It should be understood that the *S. mutans* plate was incubated in a carbon dioxide environment, and the *S. aureus* and *C. albicans* plates were incubated in an oxygen environment. The contaminated brushes were then placed in a 100% denatured ethanol bath after each use for 10 minutes. The brushes were allowed to air dry prior to each use. This procedure was repeated very day for seven days.

For quality control purposes, the following process was followed. Two brushes which had previously been used in the aforementioned procedure were removed from the 100% denatured ethanol and were allowed to air dry. Thereafter, one brush was placed in 10 ml. of nutrient broth and subsequently vortexed. The second brush was then placed in the disinfecting solution for five minutes. After five minutes, this brush was removed and placed in a 10 ml. nutrient broth and then vortexed. Utilizing a 0.01 ml. Quantitive loop, inoculant is removed from each of these brushes and separate blood agar plates are streaked for isolation with both broth inoculants. These blood agar plates, which are now indicated as being quality control plates, are incubated in oxygen for 24, 48 and 72 hours respectively, and colony counts are recorded at each point in time. These two contaminated brushes are then placed in 100% denatured ethanol after each use for 10 minutes.

Results

TEST A

The following results were obtained:

|  |  | Date | Colony Counts | | | |
|---|---|---|---|---|---|---|
|  |  | set-up | 24 h | 48 h | 72 h | Control |
|  | Disinfecting solution - Data sheet (inoculums of $1.5 \times 10^8$ CFU/ml) *S. aureus* ATCC 25923 | | | | | |
| Day 1 | 5 min/10/30 | 3/05/98 | 28/25/8 | 26/21/8 | 26/21/8 | >100 |
| Day 2 | " | 3/06/98 | >100/67/2 | >100/67/2 | >100/67/2 | " |
| Day 3 | " | 3/08/98 | 2/7/0 | 2/7/0 | 2/7/0 | " |
| Day 4 | " | 3/09/98 | 0/1/0 | 0/1/0 | 0/1/0 | " |
| Day 5 | 5 min/10/1 h | 3/11/98 | >100/4/0 | >100/4/0 | >100/4/0 | " |
| Day 6 | " | 3/12/98 | 23/6/0 | 25/6/0 | 27/6/0 | " |
| Day 7 | " | 3/13/98 | 47/11/10 | 47/11/0 | 47/12/0 | " |

-continued

S. mutans ATCC 35668

| | | | | | | |
|---|---|---|---|---|---|---|
| Day 1 | 5 min/10/30 | 3/05/98 | >100/20/0 | >100/20/0 | >100/20/2 | >100 |
| Day 2 | " | 3/06/98 | 19/47/0 | 19/47/0 | 19/47/0 | " |
| Day 3 | " | 3/08/98 | 0/0/0 | 2/0/0 | 0/0/0 | " |
| Day 4 | " | 3/11/98 | 20/44/0 | 27/64/2 | 25/59/2 | " |
| Day 5 | 5 min/10/1 h | 3/12/98 | 79/18/0 | 85/34/0 | 85/34/0 | " |
| Day 6 | " | 3/13/98 | 42/2/0 | 54/9/0 | 54/9/0 | " |
| Day 7 | " | 3/14/98 | >100/7/0 | 110/6/0 | >100/6/0 | " |

C. albicans

| | | | | | | |
|---|---|---|---|---|---|---|
| Day 1 | 5 min/10/30 | 3/05/98 | 22/15/0 | 21/15/0 | 21/15/1 | >100 |
| Day 2 | " | 3/06/98 | 38/0/0 | 38/1/2 | 38/1/2 | >100 |
| Day 3 | " | 3/08/98 | 4/1/0 | 4/3/1 | 4/3/1 | 7 |
| Day 4 | " | 3/09/98 | 10/10/0 | 10/10/0 | 10/15/0 | >100 |
| Day 5 | 5 min/10/1 h | 3/11/98 | 22/5/0 | 21/5/0 | 21/5/0 | 4 |
| Day 6 | " | 3/12/98 | 8/28/00 | 9/28/00 | 9/28/00 | >100 |
| Day 7 | " | 3/13/98 | 23/1/0 | 23/1/0 | 23/1/0 | >100 |

Quality Control (QC) brush/disinfectant

| | | Date | Colony Counts | | |
|---|---|---|---|---|---|
| | | set-up | 24 h | 48 h | 72 h |
| Day 1 | 5 min | 3/05/98 | 0/0 | 0/0 | 0/0 |
| Day 2 | " | 3/06/98 | 0/0 | 0/0 | 0/0 |
| Day 3 | " | 3/08/98 | 0/0 | 0/0 | 0/0 |
| Day 4 | " | 3/09/98 | 0/0 | 0/0 | 0/0 |
| Day 5 | 5 min/10/1 h | 3/11/98 | 0/0 | 0/0 | 0/0 |
| Day 6 | " | 3/12/98 | 0/0 | 0/0 | 0/0 |
| Day 7 | " | 3/13/98 | 0/0 | 0/0 | 0/0 |
| Day 8 | | 3/14/98 | 0/0 | 0/0 | 0/0 |

| | Date | Colony Counts | | | |
|---|---|---|---|---|---|
| | set-up | 24 h | 48 h | 72 h | Control |

Test B
Disinfecting solution -
Data sheet (inoculums of 1.5 × 10$^4$ CFU/ml)

S. aureus ATCC 25923

| | | | | | | |
|---|---|---|---|---|---|---|
| Day 1 | 5 min/10/30 | 3/20/98 | 0/0/0 | 0/0/0 | 0/0/0 | >100 |
| Day 2 | " | 3/21/98 | 1/0/0 | 1/0/0 | 1/0/0 | " |
| Day 3 | " | 3/22/98 | 0/0/0 | 0/0/0 | 0/0/0 | " |
| Day 4 | " | 3/23/98 | 1/0/0 | 1/0/0 | 1/0/0 | " |
| Day 5 | " | 3/24/98 | 0/0/0 | 0/0/0 | 0/0/0 | " |
| Day 6 | " | 3/25/98 | 0/0/0 | 0/0/0 | 0/0/0 | " |
| Day 7 | " | 3/27/98 | 0/0/0 | 0/0/0 | 0/0/0 | " |

S. mutans ATCC 35668

| | | | | | | |
|---|---|---|---|---|---|---|
| Day 1 | 5 min/10/30 | 3/20/98 | 0/0/0 | 0/0/0 | 0/0/0 | >100 |
| Day 2 | " | 3/21/98 | 0/0/0 | 0/0/0 | 0/0/0 | " |
| Day 3 | " | 3/22/98 | 0/0/0 | 0/0/0 | 0/0/0 | " |
| Day 4 | " | 3/23/98 | 0/0/0 | 0/0/0 | 0/0/0 | " |
| Day 5 | " | 3/24/98 | 0/0/0 | 0/0/0 | 0/0/0 | " |
| Day 6 | " | 3/25/98 | 0/0/0 | 0/0/0 | 0/0/0 | " |
| Day 7 | " | 3/27/98 | 0/0/0 | 0/0/0 | 0/0/0 | " |

C. albicans

| | | | | | | |
|---|---|---|---|---|---|---|
| Day 1 | 5 min/10/30 | 3/20/98 | 0/6/2 | 0/6/2 | 0/6/02 | >100 |
| Day 2 | " | 3/21/98 | 13/0/0 | 13/0/5 | 13/0/5 | " |
| Day 3 | " | 3/22/98 | 1/5/05 | 1/5/06 | 1/5/06 | " |
| Day 4 | " | 3/23/98 | 22/15/0 | 23/15/0 | 23/15/0 | " |
| Day 5 | 5 min/10/1 h | 3/24/98 | 12/5/02 | 12/5/02 | 12/5/02 | " |
| Day 6 | " | 3/25/98 | 7/4/00 | 7/4/00 | 7/4/00 | " |
| Day 7 | " | 3/27/98 | 2/1/01 | 2/1/01 | 2/1/01 | " |

-continued

| | | Quality Congrol (QC) brush/disinfectant | | | |
|---|---|---|---|---|---|
| | | Date | Colony Counts | | |
| | | set-up | 24 h | 48 h | 72 h |
| Day 1 | 5 min | 3/20/98 | 0/0 | 0/0 | 0/0 |
| Day 2 | " | 3/21/98 | 0/0 | 0/0 | 0/0 |
| Day 3 | " | 3/22/98 | 0/0 | 0/0 | 0/0 |
| Day 4 | " | 3/23/98 | 0/0 | 0/0 | 0/0 |
| Day 5 | " | 3/24/98 | 0/0 | 0/0 | 0/0 |
| Day 6 | " | 3/25/98 | 0/0 | 0/0 | 0/0 |
| Day 7 | " | 3/27/98 | 0/0 | 0/0 | 0/0 |

The above data, as provided, demonstrates conclusively that the disinfecting solution, as described herein, is effective in reducing the number of colony forming units of bacteria which are derived from a toothbrush or other dental appliance, and which may be reintroduced to the patient's oral cavity by way of the same toothbrush or dental appliance. It has been discovered, that in certain medical conditions, the subsequent reintroduction of bacteria into the oral cavity by way of contaminated dental appliances, or a toothbrush, can exasperate or further prolong the duration of an illness or disorder. The present kit, which includes this disinfecting solution, provides an effective means whereby this bacterial reintroduction can be substantially eliminated.

EXAMPLE 3

In this example, the efficacy of the mouthwash which is employed with the present invention is demonstrated.
Methods Three mouthwash test preparations were evaluated for antimicrobial properties against *Candida albicans* and *Streptococcus mutans*. Cell suspensions of each organism were exposed to three mouthwash preparations, separately, over multiple timepoints; plated on blood agar (BAP); incubated at 35° C.; and colony counts recorded at 24 and 48 hours respectively. The mouthwash test preparations contain cetylpyridinium chloride (CPC), without flavoring components, at a 1×strength made from a 50×cetylpyridinium chloride stock (CPC); A1 blue, and A2 green were provided at the working concentration. 50 μl of CPC, A1 blue, and A2 green were plated separately, as controls, to detect possible contamination of the respective mouthwash preparations. McFarland cell suspensions of *C. albicans* and *S. mutans* (ATCC 35668) were made in tryptone yeast extract broth (Sensibroth) yielding, approximate cell densities of $1.5 \times 10^8$ cells/ml. 50 μl of each organism were plated as a growth control.

Cell suspensions of both organisms were tested against the three mouthwash solutions as follows: a 1:100 mixture of cells in mouthwash was made at time zero, and 50 μL was removed immediately, and plated on a BAP. Subsequent aliquots were collected at 10 seconds, 30 seconds, 1 minute, 5 minutes, and 10 minute timepoints and plated on BAP. *C. albicans* plates were incubated in oxygen at 35 degrees Centigrade. *S. mutans* plates were incubated in carbon dioxide at 35 degrees Centigrade.
Results CPC, A1 blue, and A2 green control plates showed no contamination of the mouthwash solutions prior to testing (Table I). Growth controls of cell suspensions demonstrated recovery of viable organisms prior to exposure to mouthwash (Table 1).

1×CPC mouthwash was shown to effectively kill both *S. mutans* and *C. albicans* at as little as 10 seconds of exposure (Table 2). After 24 hours of incubation, no growth was seen on plates inoculated with A1 blue-treated *S. mutans*. However, at 48 hours, 25 colonies appeared on the 10 second plate and no growth was observed at other timepoints (Table 3). A1 blue decreased *C. albicans* growth by 3 to 4 fold, but total killing of the organism was not achieved even at 10 minutes of exposure (Table 3).

No growth was seen on plates inoculated with green-treated *S. mutans* after 24 hours of incubation, however, at 48 hours, greater than 100 colonies were present at all timepoints (Table 4). As with the A1 blue experiment, A2 green did not achieve total killing of *C. albicans* even after 10 minutes but growth inhibition was apparent by 3 to 4 fold (Table 4).

It was seen that CPC effectively killed both *S. mutans* and *C. albicans* even after a brief 10 second exposure. A1 blue was inhibitory to the growth of both organisms, however, it did not achieve total killing of *C. albicans* but was more effective against *S. mutans*. A2 green inhibited growth of both organisms but did not achieve total killing. A2 green demonstrated significantly better inhibition of *S. mutans* than A1 blue while both mouthwash preparations were comparable inhibitors of *C. albicans*.

TABLE 1

| | Control Plates | |
|---|---|---|
| Inoculum | 24 hours | 48 hours |
| CPC[1] | no growth | no growth |
| A1 Blue[1] | no growth | no growth |
| A2 Green[1] | no growth | no growth |
| *Candida albicans*[2] | >1000 colonies | same as 24 hours |
| *Streptococcus mutans*[2] | >1000 colonies | same as 24 hours |

1. 50 μl of each pre-inoculation test was plated.
2. Approximately $7.5 \times 10^6$ CFU/ml of *C. albicans* and *S. mutans* were plated as growth controls.

TABLE 2

Antimicrobial effectiveness of CPC (Cetyl Pyridinium Chloride)

| Timepoint | Candida albicans[1] | | Streptococcus mutans[2] | |
| --- | --- | --- | --- | --- |
| | colonies in 24 hrs | colonies in 48 hrs | colonies in 24 hrs | colonies in 48 hrs |
| 10 sec | none | none | none | none |
| 30 sec | none | none | none | none |
| 1 min | none | none | none | none |
| 5 min | none | none | none | none |
| 10 min | none | none | none | none |

1. approximately $7.5 \times 10^4$ CFU/ml of *C. albicans* in CPC plated on BAP at timepoints indicated.
2. Approximately $7.5 \times 10^4$ CFU/ml of *S. mutans* in CPC plated on BAP at timepoints indicated.

TABLE 3

Antimicrobial effectiveness of A1 Blue

| Timepoint | Candida albicans[1] | | Streptococcus mutans[2] | |
| --- | --- | --- | --- | --- |
| | colonies in 24 hrs | colonies in 48 hrs | colonies in 24 hrs | colonies in 48 hrs |
| 10 sec | 19 | 21 | none | 25 |
| 30 sec | 14 | 14 | none | none |
| 1 min | 08 | 08 | none | none |
| 5 min | 30–35 | 34 | none | none |
| 10 min | 10 | 11 | none | none |

1. Approximately $7.5 \times 10^4$ CFU/ml of *C. albicans* in A1 blue plated on BAP at timepoints indicated.
2. Approximately $7.5 \times 10^4$ CFU/ml of *S. mutans* in A1 blue plated on BAP at timepoints indicated.

TABLE 4

Antimicrobial effectiveness of A2 Green

| Timepoint | Candida albicans[1] | | Streptococcus mutans[2] | |
| --- | --- | --- | --- | --- |
| | colonies in 24 hrs | colonies in 48 hrs | colonies in 24 hrs | colonies in 48 hrs |
| 10 sec | 04 | 04 | none | >100 |
| 30 sec | 24 | 30 | none | >100 |
| 1 min | 20 | 18 | none | >100 |
| 5 min | 17 | 18 | none | >100 |
| 10 min | 36 | 37 | none | >100 |

1. Approximately $7.5 \times 10^4$ CFU/ml of *C. albicans* in A2 green plated on BAP at timepoints indicated.
2. Approximately $7.5 \times 10^4$ CFU/ml of *S. mutans* in A2 green plated on BAP at timepoints indicated.

EXAMPLE 4

In order to determine the relative toxicity or irritancy levels of various toothpastes and mouthwashes, a red blood cell heamolysis assay was employed to obtain information on the effects of these substances on cell membrane integrity. The Red Blood Cell assay provides a simple test system that uses easily obtainable cells and is characterized by defined and objective endpoints. The assay is rapid, inexpensive, and does not require any specialized equipment. Haemoglobin release is a useful endpoint of cell membrane integrity. It is therefore highly suitable as a screening assay in a first-order in vitro test battery for the assessment of potential toxicity to tissue, including tissues of the oral cavity.

1. Experimental Design
1.1. Objectives
  To assess the membranolytic activity of test materials. The test materials are incubated with isolated red blood cells. The degree of damage to the red blood cell membrane is quantified by spectro-photometric measurement of released haemoglobin.
1.2 Summary of Test Method
  Red blood cells are isolated concentrations of the test materials defined from results of a range finding; released hemoglobin is measured at 541 nm and the concentration resulting in 50% hemolysis relative to a totally lysed sample) calculated.
2. Test Procedure
2.1. Preparation of Red Blood Cells
  (a) Blood is collected (with a suitable anticoagulant) and diluted (4 vol; 10 vol) with PBS (see Appendix 2 for preparation of buffers). The solution is centrifuged at 11500×g at room temperature for 10 minutes and the supernatant and "buffy." layer of write blood cells carefully removed with a pasteur pipette. The packed red blood cells are suspended ended in PBS to a total volume of 10 ml and centrifuged as before. The whole process is repeated again so that a total of three "washes" is made in all.
  (b) After the final centrifugation, the packed cell volume is diluted with phosphate buffered saline (PBS) to give an approximate 2% erythrocyte suspension. However, for a packed volume of e.g. 2 ml, where the required volume of PBS added would be 98 ml, add 80 ml at this stage. The exact volume of PBS required for a 2% suspension is calculated from the optical density and adjusted accordingly.
  (c) To determine the optical density, a 1 ml sample of the erythrocyte suspension (prepared above) is diluted to 10 ml in distilled or deionised water (when using distilled water the pH should be in the range of 6.5–7.5). The desired optical density (OD) of the lysate is equivalent to 0.5 (±5%) at 541 mm in 1 cm path length cells. Distilled or deionised water is used as the blank sample. The desired volume of PBS required for the correct concentration of erythrocytes in suspension to give the normal desired extinction of 0.5 (±5%) is calculated using the following equation:

$$\frac{0.6 \text{ (optical density)} \times 80}{0.5} = 96 \text{ ml } PBS$$

EXAMPLE 2 ml (packed cell volume)+80 ml PBS $$\frac{\text{Observed } OD \times \text{original volume of } PBS}{\text{Desired } OD} = \text{Desired vol. } PBS$$

i.e. add 16 ml of PBS to the original 80 ml to give the desired total volume of suspension.
  (d) The prepared suspension can be stored at 4° C. for up to 5 days; if before the end of this period any visual signs of haemolysis are detected, then the sample should be discarded.

Red Blood Cell Haemolysis Test

Rangefinding Study: Test materials are dissolved in PBS or vehicle (Section 3) at the following fixed final assay concentrations in mg/1 (w/v):

1.0
10.0
100.0
1,000.0
10,000.0
100,000.0

(a) 1 vol of erythrocyte suspension is added to 3 vols of the test material in PBS or vehicle to give the final concentrations shown above; a single sample is used for each concentration to be tested. Assay mixtures are incubated for 60 minutes at room temperature with agitation.

(b) After the incubation period, the samples are centrifuged at approximately 10,000 gav/min and the degree of haemolysis determined spectrophotometrically at 541 nm. Results are compared to a sample totally lysed with distilled or deionised water.

Main Haemolysis Study

A minimum of 2 k concentrations adequately spaced within the concentration range derived from the rangefinding study, will be assessed to give an accurate indication of the concentration resulting in 50% haemolysis ($H_{50}$) by a standard method (calculation from graphical plots of percentage haemolysis versus concentration).

Selection of Test Concentrations:

As a result of the rangefinding study, a provisional concentration range for haemolytic effect can be identified. Initial main study concentrations are selected to span both the concentrations of maximum and minimum effect A geometric progression of selected concentrations is recommended.

Haemolysis Test:

(a) Samples are prepared in triplicate at final concentrations selected from the rangefinding study as above. Assay mixtures are incubated (3 vols sample with 1 vol erythrocyte suspension) for 60 minutes at room temperature with agitation.

(b) After the incubation period, the samples are centrifuged at approximately 10,000 gav/min and the degree of haemolysis determined in the supernatant at 541 nm.

(c) For each assay, results are expressed relative to a sample totally lysed with distilled or deionised water. A fragility control value will be determined (cells with PBS alone) and deducted from each extiction value obtained. Fragility control values should not normally exceed 5% of the totally lysed sample.

(d) Spectrophotometer blanking; vehicle containing 10% of each test material (or saturated solution) will be compared to the extinction of vehicle alone. If there is no significant difference (OD increase of less than 0.01 units) then vehicle will be used as the assay blank. If the test material causes a change in extinction, then relevant test material blanks will be employed at each concentration tested.

(e) Positive control samples should be incorporated for each blood preparation. Sodium dodecyl sulphate (SDS) of high purity (>99%) specification should be used; recommended final assay concentrations are 10 and 100 mg/l.

If the lowest rangefinding concentration tested (1.0 mg/l) produces a significant haemolysis and this can be confirmed in triplicate, then in this case the $H_{50}$ value will be defined as equal to or less than 1.0 mg/l.

If the highest rangefinding concentration tested (100,000 mg/l) fails to produce haemolysis and this can be confirmed in triplicate, then in this case the $H_{50}$ value will be defined as equal to or greater than 100,000 mg/l.

Results

The following results were demonstrated with the above described assay:

| Toothpaste: | |
|---|---|
| Test Material | % Haemolysis |
| Phosphate Buffered Saline | 0.00 |
| TP-1 | 1.34 |
| Crest ® Tartar Protection | 96.56 |
| Colgate ® Total | 84.99 |
| Peroxicare ® | 91.88 |
| Crest ® Multicare | 92.61 |

| Mouthwash: | |
|---|---|
| Test Material | % Haemolysis |
| Phosphate Buffered Saline | 0.00 |
| Scope ® | 134.79 |
| ACT ® | 83.80 |
| MW-1 | 5.05 |

| Individual Components: | |
|---|---|
| Test Materials | % Hemolysis |
| Phosphate Buffered Saline | 0.00 |
| 0.25% Sodium Fluoride | 3.31 |
| 0.05% CPC | 92.36 |
| 0.10% DHA | 3.24 |

The above results demonstrate that the compositions of the present invention, TP-1 and MW-1 cause significantly less haemolysis than other brands of toothpastes and mouthwashes, respectively. Consequently, these compositions will cause less toxicity and irritancy to oral tissues.

Therefore, it will be seen that the oral hygiene preparations, associated method, and kit for utilizing same, provides a filly dependable and practical means by which an individual can, with less toxicity or irritancy, reduce the numbers of microflora in their oral cavity and which contribute to the development of maladies such as caries, and other oral disorders. The present invention further substantially inhibits the development of other diseases which may find their path of introduction into the patient by way of contaminated oral appliances such as toothbrushes, dentures, and various orthodontic appliances as well as by contaminated toothbrushes.

The oral hygiene preparations and kit for utilizing same of the present invention further eliminates many of the deficiencies attendant with the prior art practices by providing a simple, easy kit which can be readily utilized by an individual without substantial instruction. The present oral hygiene preparations are effective, safe, pleasant tasting, and highly effective in reducing the incidence of various oral diseases. The invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. An oral hygiene method for reducing the incidence of caries in a patient, comprising: contacting the patient's teeth, and surrounding oral cavity, with a toothpaste comprising about 1.6 to about 2.6% by weight of lauroyl sarcosinate, about 0.18% to about 0.37% Cetylpyridinium Chloride, and about 0.1 to about 0.6% dehydroacetic acid, and mouthwash composition comprising about 0.05 to about 0.1% Cetylpyridinium Chloride, about 0.15 to about 0.4% lauroyl sarcosinate, about 0.1 to about 0.06% dehydroacetic acid, and about 0.01 to about 0.1% citric acid; and exposing the patient's dental appliances and toothbrush periodically to a disinfecting solution comprising about 0.06 to about 0.75% Cetylpyridinium Chloride and about 1 to 2% lauroyl sarcosinate.

2. The oral hygiene method as claimed in claim 1, wherein the toothpaste, mouthwash and disinfecting solution each have a pH of about 6.2.

3. The oral hygiene method as claimed in claim 1, wherein the patient's dental appliances and tooth brush are exposed to the disinfecting solution after being exposed to the oral cavity of the patient.

4. An oral hygiene kit, comprising:
a toothpaste for use in combination with a toothbrush; a mouthwash; and a disinfecting solution td disinfect the toothbrush, and wherein the toothpaste comprises about 1.6 to about 2.6% by weight of lauroyl sarcosinate, about 0.18% to about 0.37% Cetylpyridinium Chloride, and about 0.1 to about 0.6% dehydroacetic acid, said mouthwash comprises about 0.05 to about 0.1% Cetylpyridinium Chloride, about 0.15 to about 0.4% lauroyl sarcosinate, about 0.01 to about 0.06% dehydroacetic acid, and about 0.01 to about 0.1% citric acid; and said disinfecting solution each comprise a therapeutically effective amount of about 0.06 to about 0.75% Cetylpyridinium Chloride and about 1 to about 2% Sodium Lauroyl Sarcosinate to reduce the incidence of caries in a patient.

5. The oral hygiene kit as claimed in claim 4, wherein the therapeutically effective amount of Cetylpyridinium Chloride and the Sodium Lauroyl Sarcosinate in the toothpaste, mouthwash and disinfecting solution effectively reduces the number of bacterial flora which contribute to the development of caries.

6. The oral hygiene kit as claimed in claim 4, wherein the toothpaste comprises:
about 1.6% to about 2.6%, by weight, of Sodium Lauroyl Sarcosinate;
about 0.25% to about 0.30%, by weight of Sodium Fluoride;
about 0.1% to about 0.6%, by weight, of Dehydroacetic Acid;
about 0.18% to about 0.37%, by weight, of Cetylpyridinium Chloride;
about 30% to about 60%, by weight, of Sorbitol;
about 3% to about 10%, by weight, of Glycerin;
about 1% to about 3%, by weight, of Cellulose Gum;
about 0.3% to about 1.0%, by weight, of Titanium Dioxide;
about 0.08% to about 0.1%, by weight, of Flavors;
about 10% to about 30%, by weight, of Hydrated Silica; and
about 10% to about 30%, by weight, of water.

7. A toothpaste comprising about 1.6 to about 2.6% by weight Sodium Lauroyl Sarcosinate, Sodium Fluoride; about 0.1 to about 0.6% Dehydroacetic Acid; about 0.18% to about 0.37% Cetylpyridinium Chloride, and Glycerin, at a pH of 6.2.

8. A mouthwash comprising about 0.15 to about 0.4% Sodium Lauroyl Sarcosinate; Sodium Fluoride; about 0.01 to about 0.06% Dehydroacetic Acid; and about 0.05 to about 0.1% Cetylpyridinium Chloride, at a pH of 6.2.

9. The mouthwash of claim 8, further comprising polysorbate.

* * * * *